US012216272B2

(12) United States Patent
Rahaman et al.

(10) Patent No.: US 12,216,272 B2
(45) Date of Patent: *Feb. 4, 2025

(54) DETECTION OF OPTICAL SURFACE OF PATIENT INTERFACE FOR OPHTHALMIC LASER APPLICATIONS USING A NON-CONFOCAL CONFIGURATION

(71) Applicant: AMO Development, LLC, Irvine, CA (US)

(72) Inventors: Mohammad Saidur Rahaman, Santa Clara, CA (US); Hong Fu, Pleasanton, CA (US); Roger W. Accurso, Corning, CA (US); Zenon Witowski, Rancho Santa Margarita, CA (US)

(73) Assignee: AMO Development, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/487,027

(22) Filed: Oct. 13, 2023

(65) Prior Publication Data

US 2024/0118536 A1    Apr. 11, 2024

Related U.S. Application Data

(63) Continuation of application No. 17/643,584, filed on Dec. 9, 2021, now Pat. No. 11,789,256, which is a
(Continued)

(51) Int. Cl.
*G02B 26/08* (2006.01)
*A61B 3/13* (2006.01)
(Continued)

(52) U.S. Cl.
CPC ............ *G02B 26/0875* (2013.01); *A61B 3/13* (2013.01); *A61F 9/008* (2013.01); *G01J 1/4257* (2013.01);
(Continued)

(58) Field of Classification Search
CPC .... G02B 26/0875; G02B 27/108; A61B 3/13; A61F 9/008; A61F 2009/00855; A61F 2009/00897; G01J 1/4257
See application file for complete search history.

(56) References Cited

U.S. PATENT DOCUMENTS 5,430,509 A    7/1995    Kobayashi
6,370,422 B1   4/2002    Richards-Kortum et al.
(Continued)

FOREIGN PATENT DOCUMENTS

DE    102015002726 A1 *  9/2016  ............. A61B 3/102
WO    2005039462 A1     5/2005
(Continued)

*Primary Examiner* — Collin X Beatty (57) ABSTRACT

An ophthalmic laser system uses a non-confocal configuration to determine a laser beam focus position relative to the patient interface (PI) surface. The system includes a light intensity detector with no confocal lens or pinhole between the detector and the objective lens. When the objective focuses the light to a target focus point inside the PI lens at a particular offset from its distal surface, the light signal at the detector peaks. The offset value is determined by fixed system parameters, and can also be empirically determined by directly measuring the PI lens surface by observing the effect of plasma formation at the glass surface. During ophthalmic procedures, the laser focus is first scanned insider the PI lens, and the target focus point location is determined from the peak of the detector signal. The known offset value is then added to obtain the location of the PI lens surface.

10 Claims, 3 Drawing Sheets

Related U.S. Application Data continuation of application No. 16/112,507, filed on Aug. 24, 2018, now Pat. No. 11,215,814.

(51) Int. Cl.
   *A61F 9/008* (2006.01)
   *G01J 1/42* (2006.01)
   *G02B 27/10* (2006.01)

(52) U.S. Cl.
   CPC .. *G02B 27/108* (2013.01); *A61F 2009/00855* (2013.01); *A61F 2009/00897* (2013.01)

(56) References Cited

U.S. PATENT DOCUMENTS

| | | | |
|---|---|---|---|
| 9,445,946 | B2 | 9/2016 | Angeley et al. |
| 10,667,949 | B2 | 6/2020 | Bareket et al. |
| 10,716,705 | B2 | 7/2020 | Fu |
| 11,215,814 | B2 * | 1/2022 | Rahaman ............... G01J 1/4257 |
| 11,789,256 | B2 * | 10/2023 | Rahaman ............... G02B 7/28 |
| | | | 351/221 |
| 2010/0324543 | A1 | 12/2010 | Kurtz et al. |
| 2011/0255088 | A1 | 10/2011 | Dane et al. |
| 2011/0319875 | A1 | 12/2011 | Loesel et al. |
| 2013/0072917 | A1 | 3/2013 | Kaschke et al. |
| 2014/0104576 | A1 | 4/2014 | Bor et al. |
| 2014/0155873 | A1 | 6/2014 | Bor |
| 2014/0163891 | A1 | 6/2014 | Jo et al. |
| 2015/0141972 | A1 | 5/2015 | Woodley et al. |
| 2015/0282707 | A1 | 10/2015 | Tanabe et al. |
| 2015/0282988 | A1 | 10/2015 | Simoneau et al. |
| 2018/0339363 | A1 | 11/2018 | Lee et al. |
| 2021/0000645 | A1 | 1/2021 | Miller et al. |

FOREIGN PATENT DOCUMENTS

| | | |
|---|---|---|
| WO | 2009033107 A2 | 3/2009 |
| WO | 2012135073 A2 | 10/2012 |
| WO | 2014163891 A1 | 10/2014 |

\* cited by examiner

DETECTION OF OPTICAL SURFACE OF PATIENT INTERFACE FOR OPHTHALMIC LASER APPLICATIONS USING A NON-CONFOCAL CONFIGURATION

This application claims priority to and is a continuation of Ser. No. 17/643,584, filed Dec. 9, 2021, allowed, which claims priority to and is a continuation of Ser. No. 16/112,507, filed Aug. 24, 2018, now U.S. Pat. No. 11,215,814, issued Jan. 4, 2022. The above-referenced patent applications are incorporated herein by reference in their entireties.

BACKGROUND OF THE INVENTION

Field of the Invention

This invention relates to an ophthalmic laser system and method for laser focus point calibration, and in particular, it relates to an ophthalmic laser system employing a non-confocal optical system and related method for calibrating the depth position of the laser focus point.

Description of Related Art

An ophthalmic laser system generally includes a laser device that generates a laser beam, such as a pulsed laser beam, and a beam delivery optical system that delivers a focused spot of the laser beam into a patient's eye. The beam delivery system includes a scanner sub-system for scanning the laser focus spot in three dimensions to produce a cutting pattern within a desired volume of the eye to effectuate various desired treatments, such as tissue incisions. More specifically, the beam delivery system may include the following components, some of which are optional: a polarization beam attenuator for beam energy control, a beam sampler used to sample the beam for energy monitoring, a shutter, Z scanning optics (e.g. a lens) for changing the depth position of the laser focus spot in the eye (the depth direction or Z direction being substantially parallel to the propagation direction of the laser beam and the optical axis of the eye), X-Y scanning optics (e.g. mirrors) for scanning the laser focus spot in two transvers directions perpendicular to the depth direction, beam expander, beam rotator, various turning mirrors to change the beam direction, a focusing objective lens, and additional optical elements after the objective lens. The various components are coupled to a control system employing a computer and/or processors and/or hardware circuitry.

During the ophthalmic procedure, the patient's eye is physically coupled to the beam delivery system via a disposable patent interface (PI) device, which is attached at its proximal end to a housing of the beam delivery system and at its distal end to the surface of the eye.

The objective lens is mounted on a movement structure and moveable in the Z direction relative to the housing in order to focus the laser beam at desired depths within the eye and to vary the depth of the focus spot. An important calibration step in the operation of an ophthalmic laser system is to establish the position of the objective lens that focuses the laser beam to a known depth (Z position). In some conventional methods, calibration of the objective lens is done by placing a reflective surface in front of the objective lens at a known Z position relative to the beam delivery system housing, and using a confocal detector to measure the amount of reflected light that has traveled back through the objective lens, to determine the Z position of the objective lens that focuses the beam on the reflecting surface.

Figure 1:
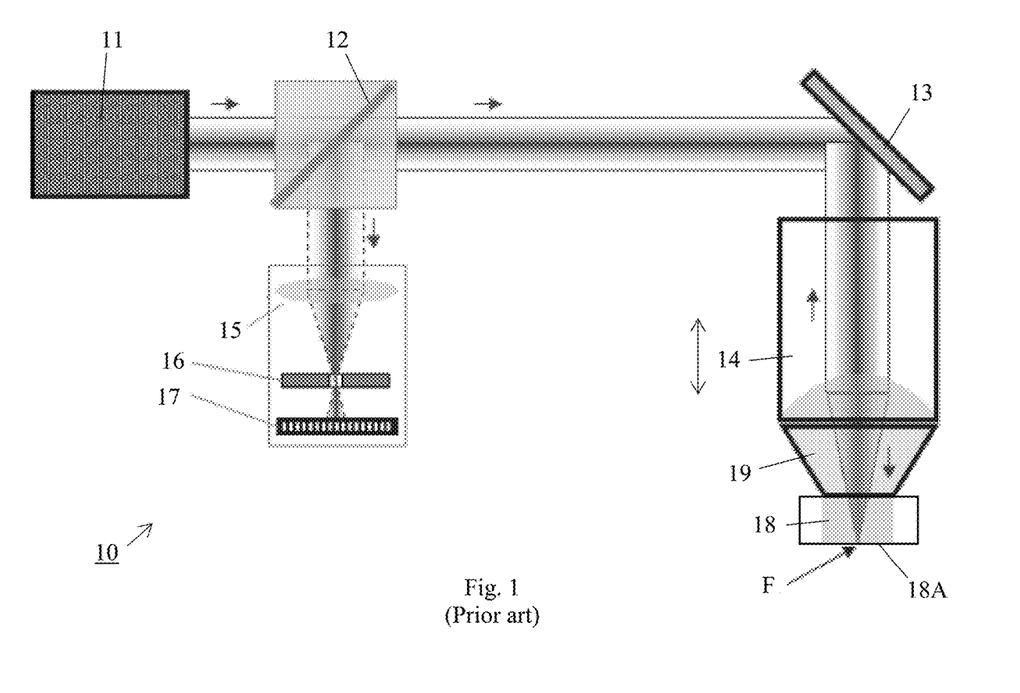
FIG. 1 schematically illustrates a portion of a conventional ophthalmic laser system that uses a confocal detection configuration for calibrating the Z position of the objective lens.

FIG. 1 schematically illustrates a portion of an ophthalmic laser system 10 that uses a confocal detection configuration for Z position calibration.

More generally, confocal microscopy is a widely used tool in biological imaging, because it significantly improves the contrast of images compared to wide field microscopy, and it allows depth segmenting. A confocal microscope is based on a double filtering operation: a certain volume inside the sample is selectively illuminated by a focused beam, and light originating from this focal volume is selectively observed using a pinhole in the detection pathway. The pinhole is located in a plane conjugated with the focal plane, and suppresses light originating from any location other than the focal volume. With this method, a point of a sample can be probed with higher contrast with respect to its surroundings. Images are built by scanning the probed focal volume inside the sample. In typical biological media, confocal microscopy allows one to obtain clear, background free images only up to a certain point.

In the system shown in FIG. 1, a laser source 11, the details of which are not shown, includes the laser device and associated optical components that are configured to produce a laser beam. A part of the laser beam passes through a beam splitter 12, and after being reflected by one more mirror 13, is focused by the objective lens 14. The laser light that exits the objective lens is reflected by a reference reflective surface 18A disposed below the objective lens 14, and the reflected light travels backwards into the objective lens. The reference surface 18A may be, for example, a surface of an optical element 18 of the PI (referred to as the PI lens), where the PI is physically attached to the beam delivery system housing and remains stationary relative to the housing. After the back-reflected light is focused by the objective lens and reflected by the mirror 13, a part of the reflected light is reflected by the beam splitter 12 into a confocal detection assembly. The confocal detection assembly includes a lens 15 (referred to as the confocal lens), a pinhole 16, and a two-dimensional light intensity detector 17. The confocal lens 15 is configured to focuses a parallel light beam to the pinhole 16, and the light that passes through the pinhole is detected by the detector 17.

Figure 2:
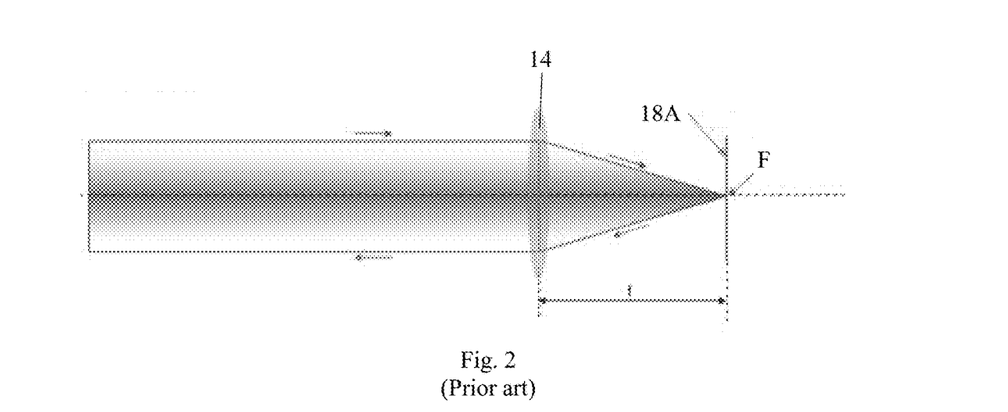
FIG. 2 schematically illustrates the principle of calibrating the Z position of the objective lens in the laser system of FIG. 1.

Referring to FIGS. 1 and 2, to calibrate the Z position of the objective lens 14, the laser source 11 is operated to generate a parallel laser beam. The objective lens 14 is continuously moved in the Z direction, and the back-reflected light that has traveled through the objective lens is continuously detected by the confocal detection assembly as the objective lens is moved. In FIG. 2, the objective lens 14 may be optically represented by a thin lens having a focal distance f, even though the objective lens is typically formed of a set of lenses. As shown in FIGS. 1 and 2, the incident laser beam is a parallel beam and is focused by the objective lens 14 to a focus point F. As the objective lens 14 is moved in the Z direction, when the focus point F is located on the reflective surface 18A (i.e., the distance between the objective lens and the reflective surface equals the focal distance of the objective lens, see FIG. 2), the light reflected by the surface 18A is focused by the objective lens 14 into a parallel beam. Then, the confocal lens 15 focuses the parallel beam onto the pinhole 16, and the light passing through the pinhole is detected by the detector 17 to produce a signal. The confocal lens 15 and the pinhole are designed such that a parallel beam will be focused to a focus spot comparable to or smaller in size than the pin hole (which is for example microns in size), so a majority of the light passes through the pinhole to be detected by the detector 17. On the other hand, when the focus point F is located away from the reflective surface 18A (not shown in FIG. 2), the light reflected from the surface 18A, after passing through the objective lens 14, will not be a parallel beam. Thus, the reflected beam that enters the confocal lens 15 is not focused onto the pinhole 16, and as a result, the amount of light that passes through the pinhole 16 to reach the detector 17 is significantly reduced. Therefore, the signal detected at the detector 17 (referred to as the auto-Z signal) peaks when the focus spot F of the objective lens is on the reflective surface 18A. By continuously moving the objective lens 14 in the Z direction and continuously detecting the auto-Z signal, the position of the objective lens that focuses the parallel incident laser beam on the reflective surface 18A is obtained. This process is sometimes referred to as detecting the optical surface of the PI. Once this objective lens position is known, the objective lens position that will place the laser focus point at any desired depth relative the reference surface 18A can be determined.

SUMMARY

The present invention is directed to an ophthalmic laser system and related method that substantially obviates one or more of the problems due to limitations and disadvantages of the related art.

An object of the present invention is to provide an ophthalmic laser system that uses a simpler structure for Z direction calibration.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides an ophthalmic laser system which includes: a laser source configured to generate a parallel light beam; an objective lens configured to focus the parallel light beam to a focus point; an objective lens movement structure configured to move the objective lens in a Z direction which is parallel to an optical path of the ophthalmic laser system; a light intensity detector; and a beam splitter disposed to guide a portion of the light beam from the laser source to the objective lens and to guide a portion of a back-reflected light beam from the objective lens to the light intensity detector, wherein the optical path is free of any lens or pinhole between the objective lens and the light intensity detector.

The ophthalmic laser system further includes a controller electrically coupled to the light detector and the objective lens movement structure, the controller being configured to control a movement of the objective lens and to analyze a corresponding signal detected by the light intensity detector to determine a position of the objective lens in the Z direction.

In some embodiments, the controller is configured to: set a power of the light beam to a first power below a plasma threshold for the patient interface optical element, and while the power is set to the first power: control the objective lens movement structure to move the objective lens in the Z direction; control the light intensity detector to measure a light that has been reflected back by the optical surface of the patient interface optical element and has passed through the objective lens; analyze a light intensity signal produced by the detector while the objective lens is moved; and determine a first position of the objective lens that corresponds to a peak position in the light intensity signal; set the power of the light beam to a second power above the plasma threshold for the patient interface optical element, and while the power is set to the second power: control the objective lens movement structure to move the objective lens in the Z direction to move the light focus point from a position outside of the patient interface optical element through the optical surface to a position inside the patient interface optical element; control the light intensity detector to measure a light that has been reflected back by the optical surface of the patient interface optical element and has passed through the objective lens; and determine a second position of the objective lens that corresponds to a sudden decrease in the light intensity signal; and calculate a difference between the first and second positions as an offset value and store the offset value.

In some embodiments, the controller is configured to: control the objective lens movement structure to move the objective lens in the Z direction; control the light intensity detector to measure a light that has been reflected back by the optical surface of the patient interface optical element and has passed through the objective lens; analyze a light intensity signal produced by the detector while the objective lens is moved; determine a first position of the objective lens that corresponds to a peak position in the light intensity signal; calculate a second position of the objective lens based on the first position, an offset value pre-stored in the controller, and a depth value, wherein the offset value represents a distance between the optical surface of the patient interface optical element and a light focus position that corresponds to the peak position in the light intensity signal; move the objective lens to the second position; and operate the laser source to scan the focus point of the light beam according to a scan pattern.

In another aspect, the present invention provides a method implemented in an ophthalmic laser system, the ophthalmic laser system comprising a laser source for generating a light beam, a moveable objective lens for focusing the light beam, a light intensity detector for detecting a light signal from the objective lens, and a controller, the method including: mounting a patient interface device on the ophthalmic laser system, the patient interface device having an optical element with a distal optical surface; using the objective lens to focus the light beam generated by the laser source to a focus point located inside the patient interface optical element; moving the objective lens to move the focus point; using the light intensity detector, detecting a back-reflected light that has been reflected by the distal optical surface of the patient interface optical element and has passed through the objective lens, to generate a light intensity signal, wherein the back-reflected light travels from the objective lens to the light intensity detector without passing through any other lens or any pinhole; analyzing the light intensity signal to determine a first position of the objective lens that corresponds to a peak position in the light intensity signal; determining a second position of the objective lens that focuses the light beam to the distal optical surface of the patient interface optical element; calculating a difference between the first and second positions of the objective lens as an offset value; and storing the offset value.

The step of determining the second position of the objective lens includes: setting a power of the light beam to be above the plasma threshold for the patient interface optical element; moving the objective lens to move the light focus point from a location outside of the patient interface optical element through the distal optical surface to a location inside the patient interface optical element; using the light intensity detector, detecting a light generated at the focus point that has passed through the objective lens; and analyzing the light intensity signal to determine the second position of the objective lens which corresponds to a sudden decrease of the light intensity signal.

In anther aspect, the present invention provides a method implemented in an ophthalmic laser system, the ophthalmic laser system comprising a laser source for generating a light beam, a moveable objective lens for focusing the light beam, a light intensity detector for detecting a light signal from the objective lens, and a controller, the method including: mounting a patient interface device on the ophthalmic laser system, the patient interface device having an optical element with a distal optical surface; using the objective lens to focus the light beam generated by the laser source to a focus point located inside the patient interface optical element; moving the objective lens to move the focus point; using the light intensity detector, detecting a back-reflected light that has been reflected by the optical surface and has passed through the objective lens, to generate a light intensity signal, wherein the back-reflected light travels from the objective lens to the light intensity detector without passing through any other lens or any pinhole; analyzing the light intensity signal to determine a first position of the objective lens that corresponds to a peak position in the light intensity signal; calculating a second position of the objective lens based on the first position, a pre-stored offset value, and a depth value, wherein the offset value represents a distance between the distal optical surface of the patient interface optical element and a light focus position that corresponds to the peak position in the light intensity signal; moving the objective lens to the second position; and operating the laser source to scan the focus point of the light beam according to a scan pattern.

It is to be understood that both the foregoing general description and the following detailed description are exemplary and explanatory and are intended to provide further explanation of the invention as claimed.

DETAILED DESCRIPTION OF PREFERRED EMBODIMENTS

As described above, the conventional optical system for calibrating the Z position of the objective lens uses a confocal detection assembly including a lens and a pinhole in front of the detector. Such a confocal system requires precise alignment of the confocal lens to the pinhole, as the confocal lens must focus the waist of the light precisely at the pinhole. This makes the system relatively complex in terms of both manufacturing of the precision components and the alignment of the components.

Embodiments of the present invention provide a simpler optical system for calibrating the Z position of the objective lens, which uses a lens imaging principle that does not use a confocal configuration.

Figure 3:
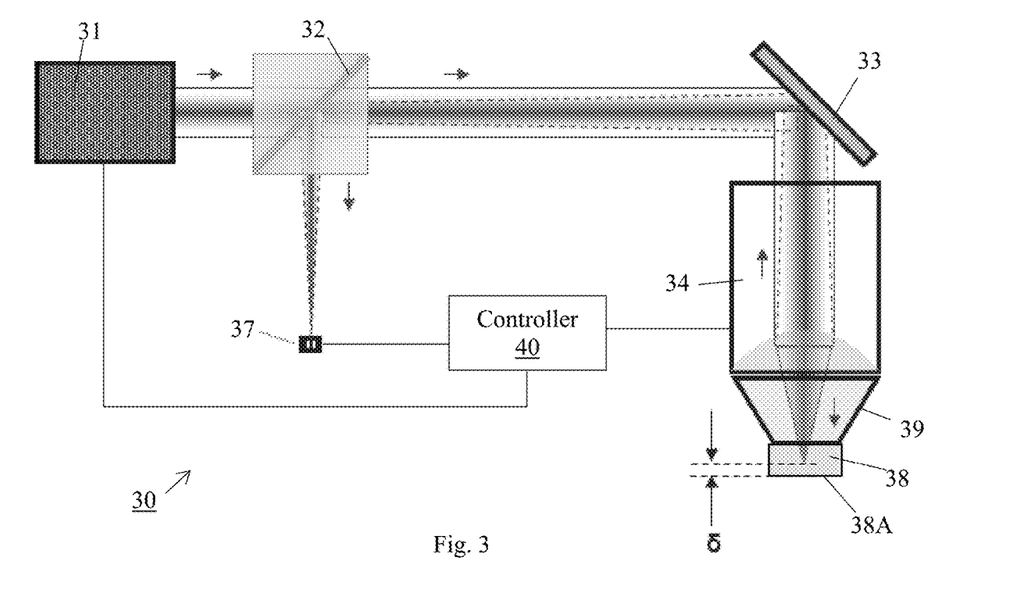
FIG. 3 schematically illustrates a portion of an ophthalmic laser system that uses a non-confocal detection configuration for calibrating the Z position of the objective lens according to an embodiment of the present invention.

FIG. 3 schematically illustrates a portion of an ophthalmic laser system 30 that uses a non-confocal detection configuration for Z position calibration according to an embodiment of the present invention. In the system shown in FIG. 3, the laser source 31, the details of which are not shown, includes a laser device and associated optical components that are configured to produces a laser beam. A part of the laser beam passes through a beam splitter 32, and after being reflected by one more mirrors 33, is focused by the objective lens 34. In a preferred embodiment, the objective lens 34 has a relatively high numerical aperture (NA), for example, approximately 0.4 or higher. The focus spot size produced by the objective lens is preferably as small as 2 µm, or 1 µm, or even smaller.

The objective lens 34 is mounted on a movement structure and moveable in the Z direction relative to the housing in order to focus the laser beam at desired depths and to vary the depth of the focus spot. The movement structure may include any suitable mechanical structure, such as a translation stage driven by a motor, etc.

A part of the laser light that exits the objective lens 34 is reflected by a reference reflective surface 38A disposed below the objective lens 34, and the reflected light travels backwards into the objective lens 34. After the back-reflected light is focused by the objective lens 34 and reflected by the mirror 33, a part of the reflected light is reflected by the beam splitter 32 onto a small two-dimensional light intensity detector 37 (e.g. a photodetector). No confocal lens or pinhole is used in front of the detector 37.

In preferred embodiments, the reference reflective surface 38A is the distal surface of an optical element 38 of the PI (referred to as the PI lens), i.e. one of the two surface of the PI lens that is located farther away from the objective lens. The PI lens may be a piece of flat glass, or it may have one or two curved surfaces. The PI is physically attached to the beam delivery system housing and remains stationary relative to the housing. FIG. 3 schematically illustrates a part of the housing 39, and the PI lens 38, but the rest of the housing and the PI are not shown. While the PI lens is transparent, in practice, its surfaces reflect a small portion (e.g. a few percent) of the beam back to the optical system. This reflected beam is used to calibrate the Z position of the objective lens.

Figure 4A:
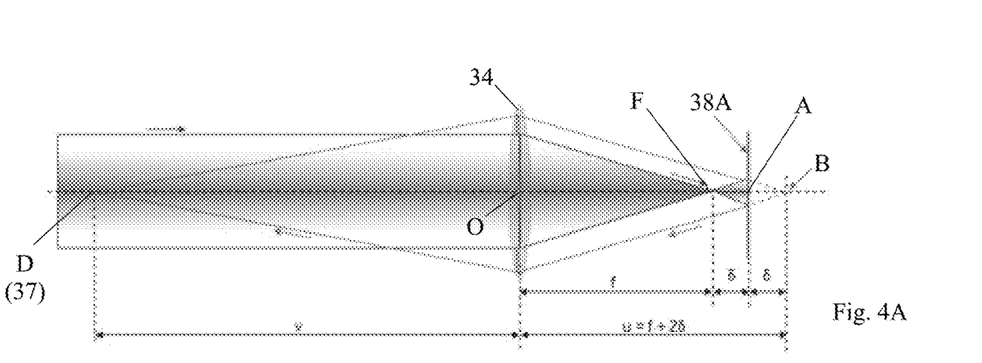
FIGS. 4A and 4B schematically illustrate the principle of calibrating the Z position of the objective lens in the laser system of FIG. 3.
Figure 4B:
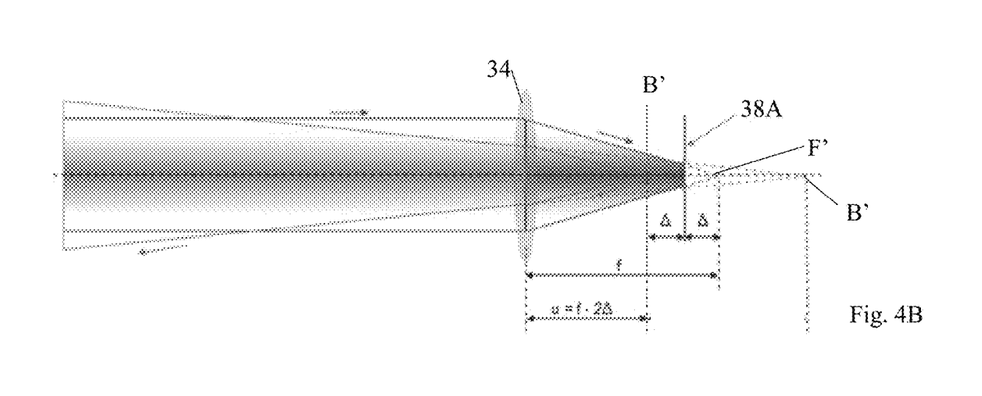

The principle of Z position calibration in the laser system of FIG. 3 is described below with reference to the schematic illustration in FIGS. 4A and 4B. In FIGS. 4A and 4B, the objective lens 34 is optically represented by a thin lens having a focal distance f, although the objective lens is typically formed of a set of lenses. It should be noted that FIGS. 4A and 4B are intended to explain the relevant optical principles; the various distances depicted in the figures are not to scale.

FIG. 4A illustrates a situation where the objective lens 34 focuses the parallel incident beam to a focus point F located between the objective lens 34 and the distal surface 38A of the PI lens 38, and inside the PI lens. In other words, the distal surface 38A is located beyond the focal plane of the objective lens 34. The forward propagating light diverges after the focus point F and is then reflected by the reflective surface 38A. To the objective lens 34, the reflected light appears to originate from a point B behind the reflective surface 38A, the point B being the mirror image of the focus point F with respect to the reflective surface 38A. The distance from the equivalent origin B to the objective lens 34 is u=f+2δ (Equation (1)), where δ=FA is the offset between the focus point F and the distal surface 38A of the PI lens. The reflected light from the equivalent origin B is focused by the objective lens 34 to an image point D at a finite distance v from the objective lens. The detector 37 is located at the image point D, and no other lens is disposed between the objective lens 34 and the detector 37. In the laser system 30, the distance DA between the location D of the detector 37 and the reflective surface 38A is a constant because both the detector and the reflective surface 38A are fixed with respect to the system housing, i.e., DA=v+f+δ, or DA≈v+f (Equation (2)) when δ is much smaller than both v and f (discussed later) and can be ignored. In other words, v can be treated as a fixed value determined by the hardware configuration.

Using Equations (1) and (2) and the following lens formula for a thin lens (Equation (3)), $$\frac{1}{u}+\frac{1}{v}=\frac{1}{f},$$

where u is the object distance and v is the image distance, and taking into consideration that δ is much smaller than both v and f and that f is much smaller than v (discussed later), one obtains $$\delta \approx \frac{f^2}{2v} \quad \text{(Equation (4))}$$

The above equations are for focusing in the air. Since the focus point F is located inside the PI lens 38, the refractive index n of the PI lens material is taken into consideration, and one obtains $$\delta \approx n \cdot \frac{f^2}{2v} \quad \text{(Equation (5))}$$

The point inside the PI lens 38 at the distance δ from the distal surface 38A, where δ satisfies Equation (5), is referred to as the target focus position for convenience.

It should be understood that in the above equations, the various distances are the distances along the optical path; the optical path may be folded by mirrors or beam splitters.

In some embodiments of the laser system 30, the focal distance f, i.e. the equivalent focal length of the objective lens 34, is a few mm, e.g. approximately 4 mm. Meanwhile, the distance DA from the detector 37 to the distal surface 38A of the PI lens, i.e., DA=v+f (ignoring δ), may be several hundreds of mm, because the choice of the detector location is not constrained and the image distance v may be lengthened if desired by folding the optical path with mirrors. In one particular embodiment, where the image distance v is approximately 500 mm, the equivalent focal length f is 3.92 mm, and the refractive index of the PI lens (glass) is n=1.45, Equation (5) gives δ≈22 μm. These values confirm that δ is much smaller than both v and f (by at least a factor on the order of 100) and that f is much smaller than v (by a factor on the order of 100).

When the objective lens 34 focuses the laser beam at positions other than the target focus position, the back-reflected light will not be focused on the detector 37 at the point D, but will be focused before it, after it, or not be focused at all. FIG. 4B schematically illustrates an example where the focus point F' is located beyond the reflective surface 38A, i.e. outside of the PI lens 38. The light from the objective lens 34 converges as it strikes the reflected surface 38A and is reflected by it; therefore, to the objective lens 34, the back-reflected light appears to originate from a point B' in front of the reflective surface 38A, the point B' being the mirror image of the focus point F' with respect to the reflective surface 38A. Since the distance from the point B' to the objective lens 34 is shorter than the focal distance, the back-reflected light remains divergent after it passes through the lens 34. As illustrated in FIG. 4B, the distance from the focus point F' to the reflective surface 38A is denoted Δ; the back-reflected light has an object distance u=f−2Δ, and forms a virtual image at a point B' behind the lens 34.

To summarize, the back-reflected light from the distal surface 38A of the PI lens 38 will only form a well focused real image on the detector 37 when the objective lens 34 focuses the parallel beam to the target focus position at δ. The detector 37 has a relatively small effective detection area, such as about 1 mm² or smaller. Having a small effective detection area refers to the detector either having a physically small detection area or being controlled to detect light falling within a small area. As a result, when the back-reflected light is not focused on the detector, substantial portions of the reflected light will not fall on the effective detection area and the detected light intensity will decrease significantly. Therefore, the light intensity signal detected at the detector 37 (the auto-Z signal) peaks when the objective lens focuses the parallel beam to the target focus position. Thus, by continuously moving the objective lens 34 in the Z direction and continuously detecting the auto-Z signal, the position of the objective lens that corresponds to the target focus position is determined. The system can achieve a sub-micron depth resolution of the Z position detection. As noted earlier, the objective lens 34 is typically formed of a set of lenses even though it is optically represented by a thin lens in the above analysis. Accordingly, moving the objective lens in the Z direction may include moving one or more of the lenses in the set of lenses so that the optical effect is that the thin lens representing the objective lens is moved in the Z direction.

Once the objective lens position corresponding to the target focus point is known, and given the knowledge of the value δ, the objective lens position that places the laser focus point at the distal surface 38A of the PI lens can be determined, since the focus point is moved by the same amount as the movement of the objective lens. Further, the objective lens position that will place the laser focus point at any desired depth relative to the distal surface 38A of the PI lens can also be determined.

From FIG. 3, it can be seen that the principle of Z position calibration applies equally when the reflective surface 38A is the proximate surface of the PI lens, in which case the target focus point F is located in the air at a distance δ from the proximate surface. But because the depths of the anatomical structures of the eye are more directly related to the distal surface of the PI lens, it is more desirable to measure the target focus point relative to the distal surface.

For a given laser system, the value δ that defines the target focus position is fixed, as it is related to the focal length f of the objective lens and the fixed distance DA from the detector 37 to the surface 38A by Equation (5). While in principle the value δ for a given laser system can be calculated from Equation (5), in practice, the fixed distance DA may be cumbersome to measure. Thus, rather than calculating the value δ from Equation (5), the value δ may be empirically determined using the following process. In this method, the location of the distal surface of the PI lens is determined by using a high power beam to cause plasma formation at the surface of the PI lens.

Figure 5:
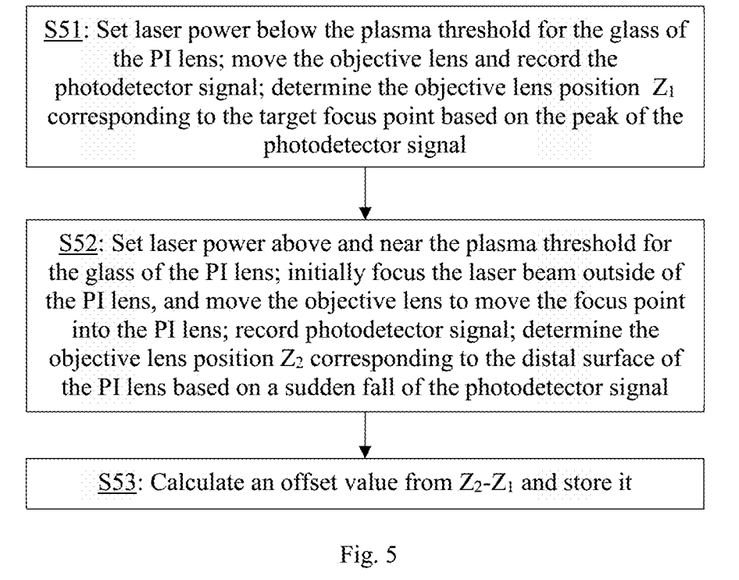
FIG. 5 schematically illustrates a method for calibrating the Z position of the objective lens in the laser system of FIG. 3.

Referring to FIG. 5, first, the objective lens position corresponding to the target focus point is determined by moving the objective lens in the Z direction and recording the auto-Z signal measured by the detector 37, as described earlier (step S51). The objective lens position corresponding to the peak of the auto-Z signal is determined and denoted $Z_1$. In this step, the laser power is set to be below the plasma threshold for the glass of the PI lens. Preferably, the objective lens position is moved in the deep-to-shallow direction (i.e. in the upward direction in the orientation of FIG. 3). For example, the laser focus point may be initially placed outside the PI lens 38 beyond the distal surface 38A, and the objective lens is moved in an appropriate direction to move the focus point upwards until the focus point moves into the PI lens and past the target focus position, while the peak of the detector signal is observed to determine $Z_1$.

Then, the laser power is set to be above and near the plasma threshold for the glass of the PI lens, and the objective lens is initially set at a position that places the laser focus point outside of the PI lens 38 (beyond the surface 38A, i.e. in the air) and then moved in the deep-to-shallow direction, while the detector signal is recorded (step S52). When the laser focus point is moved from air into the PI lens, the detector signal will suddenly fall when the laser focus touches the glass surface due to plasma formation in the glass. For example, the signal may be slow-varying and then suddenly fall by 15% or more (for example, as much as 40% in some instances) within a Z range of 1 μm. This sudden fall is believed to be caused by the damage (burn) at the glass surface which scatters the light. The objective lens position corresponding to the sudden fall of the detector signal is determined and denoted $Z_2$ (step S52). This position corresponds to the location of the distal surface of the PI lens. The value δ is calculated as the differences between the two positions of the objective lens: $\delta = Z_2 - Z_1$ (step S53).

Figure 6:
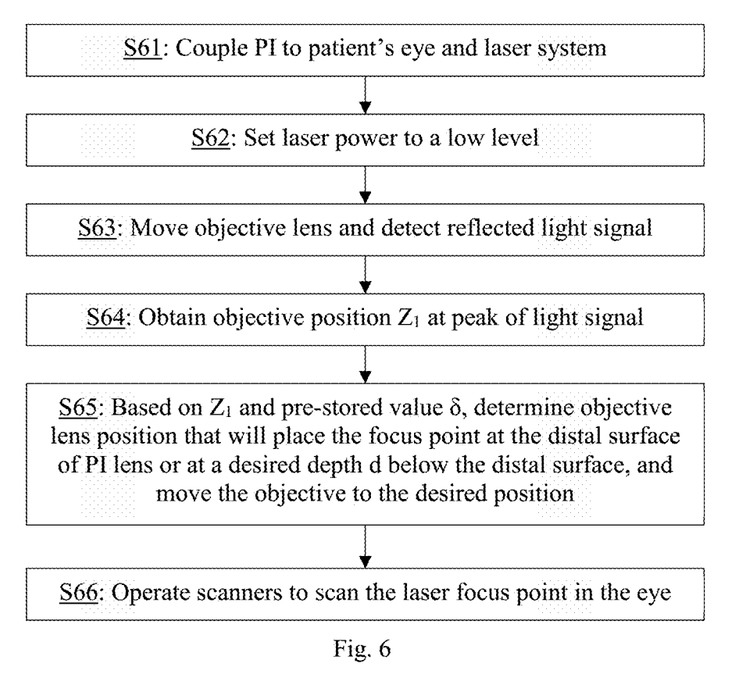
FIG. 6 schematically illustrates a method for calibrating the Z position of the objective lens and performing ophthalmic procedure using the laser system of FIG. 3.

The above method shown in FIG. 5 is performed after the laser apparatus is manufactured, and may be performed from time to time during system maintenance, but is not performed for each ophthalmic procedure. During an actual ophthalmic procedure, it is only necessary to determine the objective lens position that corresponds to the target focus position. More specifically, as shown in FIG. 6, after the PI is coupled to the patient's eye and to the housing of the laser system 30 (step S61), the laser power is set to a low level that does not cause any tissue modification in the eye (step S62), and the objective lens 34 is moved while the reflected light signal is detected by the detector 37 (step S63). The detected signal is analyzed to identify the objective lens position (denoted $Z_1$) that correspond to the peak of the detected signal (step S64). Based on the position $Z_1$ and the known value δ, which has been determined beforehand and stored in the system, the objective lens position $Z_0$ that will place the laser focus point at the distal surface of the PI lens can be calculated by $Z_0 = Z_1 + \delta$, and the objective lens position Z that will place the laser focus point at a desired depth d below the distal surface of the PI lens can be calculated by $Z = Z_1 + \delta + d = Z_0 + d$. This relationship is used to move the objective lens to any desired depth in the eye (step S65). A scanner assembly in the laser source 31 can then be operated to scan the focus point in three dimensions within the eye according to desired scan patterns (step S66).

The above methods may be performed automatically using a controller 40 which is electrically coupled to the laser source 31, the detector 37, and the movement structure of the objective lens 34. The controller may include suitable electrical circuitry, and/or microprocessors, and/or a computer, along with associated memory storing computer-readable program instructions.

An advantage of the system shown in FIG. 3 is that it eliminates the pinhole and confocal lens of the confocal detection system. This increases the robustness of the system as it uses fewer components, and relaxes the associated alignment requirement. Even though it does not use a confocal system, the system still has the flexibility that the detector can be located at any convenient location along the optical path. The system can achieve approximately the same precision in Z position determination as using a confocal system.

The glass burning effect, i.e. the phenomenon of light behavior change due to plasma formation at the glass surface, described above in connection with step S52 of the Z position calibration method, may also be used for other purposes in an ophthalmic laser system.

For example, the glass burning phenomenon may be used by itself to determine the position of the PI lens surface. In other words, step S52 described above may be performed, without performing step S51, to determine the objective lens position which corresponds to the focus point being placed at the PI lens surface. This position may then be used as a reference position in actual ophthalmic procedure to focus the laser beam to any desired depth below the PL lens surface. This method may be employed in an ophthalmic laser system that uses a non-confocal configuration such as that shown in FIG. 3, or a confocal configuration such as that shown in FIG. 1.

Moreover, this method may even be used with an external photodetector, i.e., a detector that is not located inside the physical housing of the ophthalmic laser system, by pointing the photodetector at the surface of the PI lens. It has been observed that when the laser focus point is moved from the air and reaches the glass surface, the light emitted from the glass surface in other directions (not just toward the objective lens) changes suddenly. This sudden change may be detected using the external photodetector to determine the Z position of the objective lens that focuses the beam at the PI lens surface.

In another example, the glass burning phenomenon may be used to check the health of the laser system. In a well maintained laser system, the threshold values of various system parameters, such as the pulse power setting, that would produce glass burning of the PI lens can be determined. Then, at a later time, such as after the system is shipped to a different location, the glass burning procedure is repeated at the threshold values of the system parameters. If the glass burning occurs as expected, then it indicates that the laser system is in optimum condition. Conversely, if the glass burning does not occur, then it indicates that the laser system is not in optimum condition. Such a procedure may be performed using a confocal configuration or non-confocal configuration, or using an external photodetector as described above.

The optical system with a non-confocal configuration as shown in FIG. 3 may also be used to achieve a microscope imaging system that does not employ a confocal lens and a pinhole. Similar to the confocal microscopy technique, the objective lens focuses the illumination light to a small volume inside the sample, and light originating from this focal volume is focused by the objective lens onto the small detector, without using a confocal lens or pinhole. Images are built by scanning the probed focal volume inside the sample. This technique can achieve similar results as confocal microscopy. The technique is applicable for high NA objective lens microscope since such objective lens decrease the depth of field. Thus, for a very small focal displacement, a very large beam diameter is expected at the detector plane. As a result, only reflected light from a very small focal field is detected by the detector, achieving a similar effect as confocal microscopy.

It will be apparent to those skilled in the art that various modification and variations can be made in the ophthalmic laser system and related Z position calibration method of the present invention without departing from the spirit or scope of the invention. Thus, it is intended that the present invention cover modifications and variations that come within the scope of the appended claims and their equivalents.

What is claimed is:

1. A method implemented in an ophthalmic laser system, the ophthalmic laser system comprising a laser source for generating a light beam, a moveable objective lens for focusing the light beam, a light intensity detector for detecting a light signal from the objective lens, and a controller, the method comprising:
   mounting a patient interface device on the ophthalmic laser system, the patient interface device having an optical element with a distal optical surface;
   using the objective lens to focus the light beam generated by the laser source to a focus point located inside the patient interface optical element;
   moving the objective lens to move the focus point;
   using the light intensity detector, detecting a back-reflected light that has been reflected by the distal optical surface of the patient interface optical element and has passed through the objective lens, to generate a light intensity signal, wherein the back-reflected light travels from the objective lens to the light intensity detector without passing through any other lens;
   analyzing the light intensity signal to determine a first position of the objective lens that corresponds to a peak position in the light intensity signal;
   determining a second position of the objective lens that focuses the light beam to the distal optical surface of the patient interface optical element;
   calculating a difference between the first and second positions of the objective lens as an offset value; and
   storing the offset value.

2. The method of claim 1, wherein the step of determining a second position of the objective lens includes:
   setting a power of the light beam to be above the plasma threshold for the patient interface optical element;
   moving the objective lens to move the light focus point from a location outside of the patient interface optical element through the distal optical surface to a location inside the patient interface optical element;
   using the light intensity detector, detecting a light generated at the focus point that has passed through the objective lens; and
   analyzing the light intensity signal to determine the second position of the objective lens which corresponds to a sudden decrease of the light intensity signal.

3. The method of claim 1, wherein the light intensity detector has an effective detection area of 1 mm$^2$ or less.

4. The method of claim 1, wherein the focus point has a size of 2 μm or less.

5. The method of claim 1, wherein the objective lens has a numerical aperture of 0.4 or higher.

6. A method implemented in an ophthalmic laser system, the ophthalmic laser system comprising a laser source, a moveable objective lens, and a light intensity detector for detecting a light signal from the objective lens, the method comprising:
   mounting a patient interface optical element on a housing of the ophthalmic laser system;
   generating a light beam by the laser source;
   focusing the light beam to a focus point by the objective lens;
   setting a power of the light beam to a predetermined power;
   while the power of the light beam is set to the predetermined power, moving the objective lens relative to the housing in a Z direction to move the focus point from a position outside of the patient interface optical element through an optical surface of the patient interface optical element to a position inside the patient interface optical element;
   while moving the objective lens in the Z direction, controlling the light intensity detector to measure a light that has been reflected or scattered by the optical surface; and
   based on a light intensity signal measured by the light intensity detector during movement of the objective lens, determining whether or not a sudden change in the light intensity signal occurred which indicates that a glass burn has occurred at the optical surface of the patient interface optical element.

7. The method of claim 6, wherein the predetermined power is above a plasma threshold for the patient interface optical element such that the light beam is configured to burn the optical element when the focus point is inside the optical element, the method further comprising:
   upon detecting a sudden change in the light intensity signal measured by the light intensity detector, determining a position of the objective lens that corresponds to the sudden change in the light intensity signal; and
   storing the determined position of the objective lens as a reference position corresponding to a Z direction position of the optical surface.

8. The method of claim 6, further comprising determining whether or not the ophthalmic laser system is in an optimum condition based on whether or not a glass burn has occurred.

9. The method of claim 6, wherein the optical surface is a distal optical surface of the patient interface optical element.

10. The method of claim 6, further comprising, by a beam splitter, guiding a portion of the light beam from the laser source to the objective lens and guiding a portion of a back-reflected light beam, which has been reflected back by the optical surface of the patient interface optical element and has passed through the objective lens, to the light intensity detector.

* * * * *